United States Patent
King et al.

[11] Patent Number: 6,132,582
[45] Date of Patent: Oct. 17, 2000

[54] SAMPLE HANDLING SYSTEM FOR A MULTI-CHANNEL CAPILLARY ELECTROPHORESIS DEVICE

[75] Inventors: Howard Gregg King, Berkeley; John Shigeura, Fremont; Eric S. Nordman, Palo Alto; Sean Matthew Desmond, Belmont, all of Calif.

[73] Assignee: The Perkin-Elmer Corporation, Foster City, Calif.

[21] Appl. No.: 09/152,590

[22] Filed: Sep. 14, 1998

[51] Int. Cl.[7] .................... G01N 27/26; G01N 27/447
[52] U.S. Cl. ................ 204/604; 204/453; 422/65; 422/67; 422/100
[58] Field of Search ................ 422/100, 65, 63, 422/102; 204/451, 452, 453, 455, 601, 602, 603, 604, 605

[56] References Cited

U.S. PATENT DOCUMENTS

| | | | |
|---|---|---|---|
| 4,811,218 | 3/1989 | Hunkapiller et al. | 204/461 |
| 5,274,240 | 12/1993 | Mathies et al. | 204/603 X |
| 5,356,525 | 10/1994 | Goodale et al. | 204/602 |
| 5,372,695 | 12/1994 | Demorest | 204/604 X |
| 5,439,578 | 8/1995 | Dovichi et al. | 204/603 |
| 5,516,409 | 5/1996 | Kambara | 204/603 |

FOREIGN PATENT DOCUMENTS

| | | |
|---|---|---|
| 0854362 | 7/1998 | European Pat. Off. |
| 2628215 | 9/1989 | France . |
| 4230354 | 3/1993 | Germany . |
| WO9803862 | 1/1998 | WIPO . |

OTHER PUBLICATIONS

Woolley et al., "High–Speed DNA Genotyping Using Microfabricated Capillary Array Electrophoresis Chips," *Anal. Chem.* 69(11):2181–2186 (Jun. 1, 1997).

*Primary Examiner*—Jill Warden
*Assistant Examiner*—John S. Starsiak, Jr.
*Attorney, Agent, or Firm*—Paul D. Grossman

[57] ABSTRACT

A sample handling system in a multi-channel capillary electrophoresis apparatus is disclosed. The sample handling system includes a work surface for supporting a plurality of samples located at a plurality of work surface coordinates and a sample loading assembly comprising a plurality of loading wells. At least one of the loading wells includes a capillary fixedly positioned therein. The system further includes a programmable sample transfer device for automatically transferring a sample from a work surface coordinate to a loading well. The invention further includes methods for using the sample handling system.

10 Claims, 11 Drawing Sheets

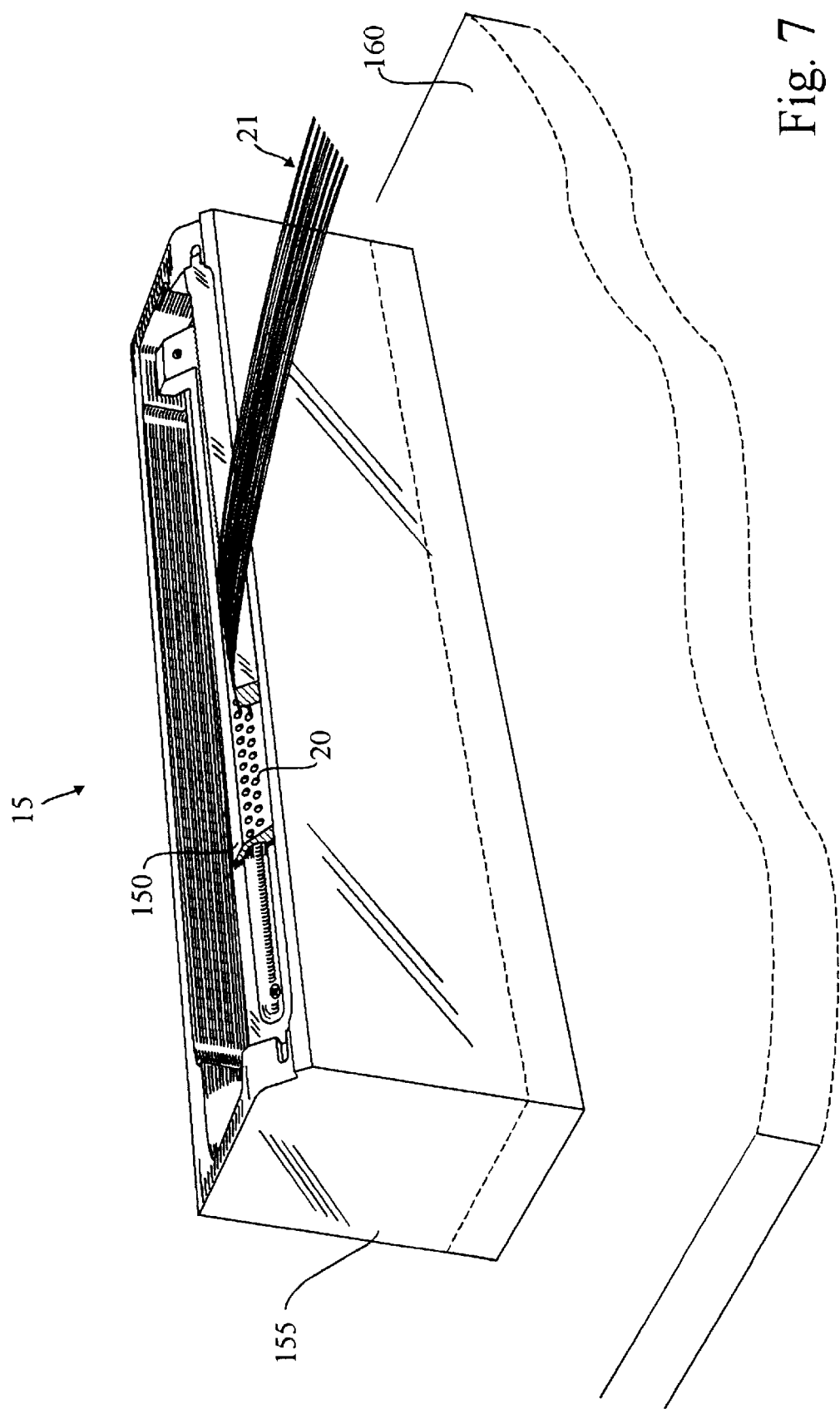

SAMPLE HANDLING SYSTEM FOR A MULTI-CHANNEL CAPILLARY ELECTROPHORESIS DEVICE

FIELD OF THE INVENTION

This invention relates to apparatus and methods useful for biochemical analysis. More specifically, this invention relates to an automated capillary electrophoresis apparatus useful for the simultaneous analysis of multiple samples, and methods for using such apparatus.

BACKGROUND

Capillary electrophoresis is a powerful analytical separation technique that brings speed, quantitation, reproducibility and automation to the inherently highly resolving but typically labor intensive methods of electrophoresis (e.g., *Capillary Electrophoresis Theory and Practice*, Grossman and Colburn, eds., Academic Press (1992)). While early capillary electrophoresis systems utilized only a single capillary tube, multi-channel systems have been developed to provide increased throughput (e.g., Mathies et al., U.S. Pat. No. 5,247,240; Dovichi and Zhang, U.S. Pat. No. 5,439,578; Kambara, U.S. Pat. No. 5,516,406; Takahashi, et al., Anal. Chem., 66:1021–1026 (1994)). Such multi-channel systems are particularly attractive for use in large scale DNA sequencing projects.

In conventional multi-capillary capillary electrophoresis systems, samples are introduced in the capillaries by dipping the capillary inlets into samples contained in a plurality of sample reservoirs. However, this method of sample introduction has several disadvantages, particularly for applications requiring a high degree of automation, throughput and reliability. First, these existing systems require a one-to-one correspondence between a given sample well location and a given capillary tube. That is, samples located in a given sample well will always be analyzed by a given corresponding capillary tube. This is problematic because if a capillary tube becomes non-operational, samples located in wells corresponding to that capillary tube will not be analyzed until that capillary is replaced. Second, in order for the capillary inlets to be dipped into the sample wells, the pitch, or spacing, of the capillary inlets must match the pitch of the sample wells. This constrains the sample well formats that may be used, and requires the capillary spacing to be dictated by the sample well configuration rather than the requirements of the analyzer. Also, because existing sample handling systems rely on the capillary tubes to be dipped into a sample well, these systems require discrete capillaries to be used rather than capillaries formed in a monolithic substrate. Finally, existing sample handling systems require a relative motion between the capillary tubes and the sample well after the sample has been injected into the capillary tubes, i.e., the capillary is removed from the sample wells, or the sample wells are removed from the capillary tubes. This relative motion may disrupt the injected sample as a result of agitation and/or evaporation such that electrophoretic resolution of the sample components is compromised.

Thus, it would be desirable to provide a sample handling system for a multi-channel capillary electrophoresis device that addresses the above disadvantages of traditional devices.

SUMMARY

The present invention is directed towards our discovery of an improved sample handling system for a multi-channel capillary electrophoresis device.

In a first aspect, the invention provides an apparatus comprising (1) a work surface for supporting a plurality of samples located at a plurality of work surface coordinates; (2) a sample loading assembly comprising a plurality of loading wells, wherein at least one of the loading wells includes a capillary fixedly positioned therein; and (3) a programmable sample transfer device for transferring a sample from a work surface coordinate to a loading well.

Various aspects of the above-described invention achieve one or more of the following important advantages over known sample handling systems for use with a multi-channel capillary electrophoresis device. In particular, the sample handling system of the invention (1) does not require a one-to-one correspondence between a given sample well location and a given capillary tube; (2) decouples a spatial arrangement of sample wells from a spatial arrangement of capillary inlets; (3) is adaptable for use with capillaries formed in a monolithic substrate; and (4) eliminates the requirement for relative motion between the capillary tubes and a sample well.

These and other features and advantages of the present invention will become better understood with reference to the following description, drawings, and appended claims.

BRIEF DESCRIPTION OF THE DRAWINGS

FIG. 7 shows a preferred loading assembly according to the present invention.

DETAILED DESCRIPTION OF THE PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications, and equivalents, which may be included within the invention as defined by the appended claims.

I. DEFINITIONS

Unless stated otherwise, the following terms and phrases as used herein are intended to have the following meanings:

The term "sample" refers to any material to be transferred between the work surface and the loading wells by the programmable sample transfer device. While samples are typically fluids, they may also be solids and/or suspensions of solids in fluids. Exemplary samples include, but are not limited to, samples to be electrophoretically analyzed, internal standards, wash solutions, buffer solutions, electrophoresis media, and the like.

The term "capillary" or "capillary tube" refers to tubes or channels or other structure capable of supporting a volume of separation medium suitable for carrying out an electrophoretic separation. The geometry of a capillary may vary widely and includes tubes with circular, rectangular or square cross-sections, channels, groves, plates, and the like, and may be fabricated by a wide range of well known technologies. An important feature of a capillary for use with the invention is the surface-to-volume ratio of the capillary lumen. High values of this ratio permit efficient dissipation of the Joule heat produced in the separation medium during electrophoresis. Preferably, ratios in the range of about 0.4 to 0.04 $\mu m^{-1}$ are employed. These ratio values correspond to the surface-to-volume ratios of tubular capillaries with circular cross-sections having inside diameters in the range of about 10 $\mu m$ to about 100 $\mu m$.

The term "well" as used herein refers to structure for confining a material to a defined location, and for separating the material from other materials. Exemplary wells include but are not limited to mechanical receptacles, surface tension barriers, slots, channels, and the like.

II. SAMPLE HANDLING SYSTEM

Figure 1:
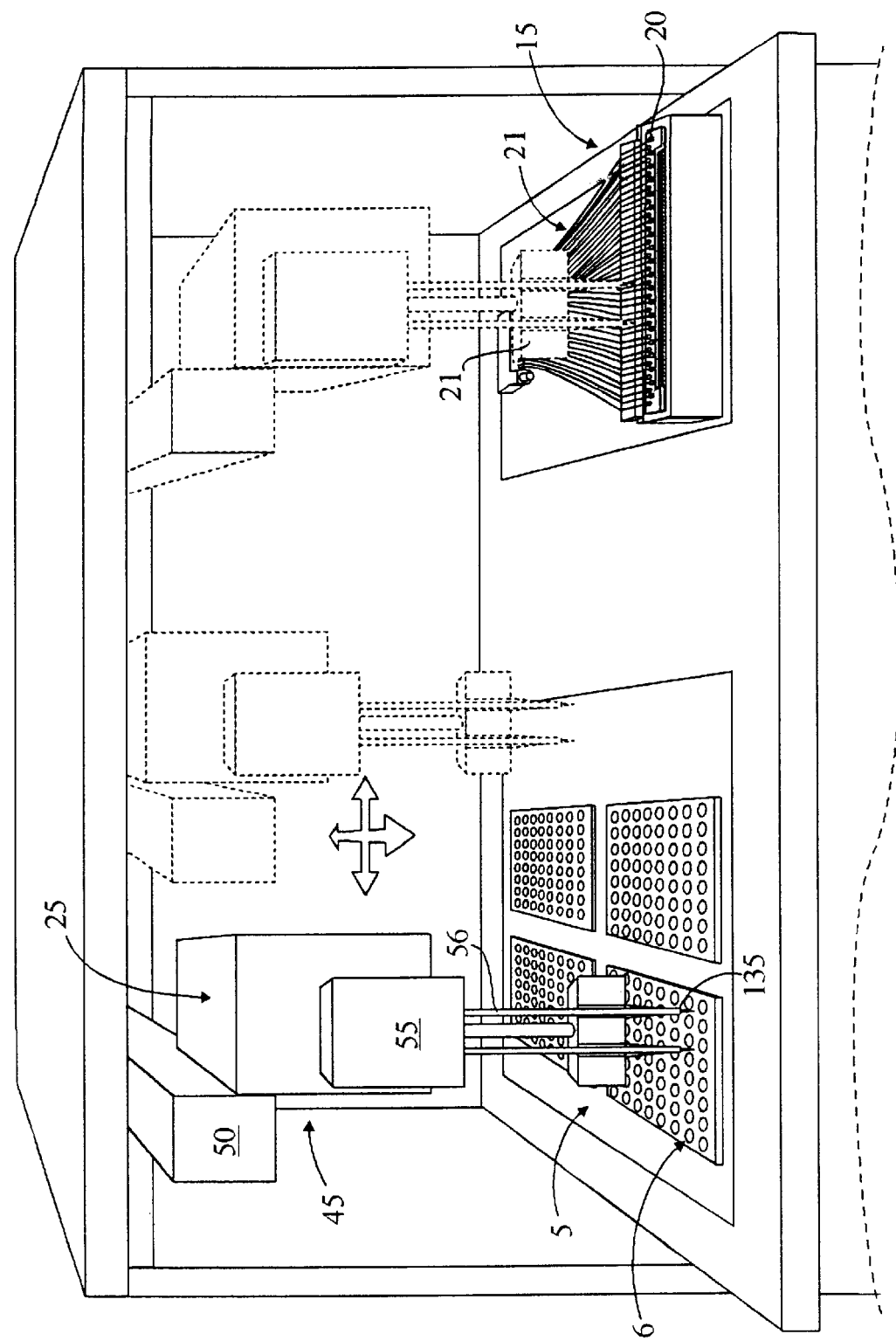
FIG. 1 shows a preferred sample handling system according to the present invention.

Generally, referring to FIG. 1, the sample handling system of the present invention comprises a work surface 5 for supporting a plurality of samples located at a plurality of addressable work surface coordinates, e.g., sample wells 6 containing samples to be electrophoretically analyzed; a sample loading assembly 15 comprising a plurality of loading wells 20, each well in fluid communication with a corresponding capillary tube 21; and a programmable sample transfer device 25 for transferring samples from the work surface to the loading wells. The material transfer device may be programmed such that a one-to-one correspondence between a work surface location and a loading well is not required.

A. Work Surface

The work surface 5 of the invention provides a location at which a plurality of samples may be stored prior to their transfer to the sample loading assembly 15. Samples are stored on the work surface at work surface coordinates such that the programmable sample transfer device 25 may automatically locate and access each sample independently, e.g., samples are located in sample wells 6 located at a plurality of addressable locations. Preferably, in order to prevent evaporation, the sample is dissolved in a solvent having a low volatility, e.g., formamide.

Preferably, the work surface is organized to accommodate multiple containers arranged in conventional formats. Generally, the containers are located on the work surface such that they may be easily replaced by a user. Exemplary container formats include microtiter plates having 96, 384 or 1536 wells arranged in a rectangular array. The containers may be open or closed. For example, a 96-well plate may be covered with a pierceable cover, e.g., a polymeric film.

The work surface may be temperature controlled, i.e., the work surface may be heated or cooled. In one preferred embodiment, the work surface is cooled in order to slow the decomposition of the samples. Alternatively, the work surface, or portions thereof, may be heated to prepare a sample for electrophoretic analysis, e.g., a nucleic acid sample may be denatured by exposure to elevated temperature prior to electrophoresis. In addition, the humidity of the environment surrounding the work surface may be controlled to reduce sample evaporation.

Figure 2:
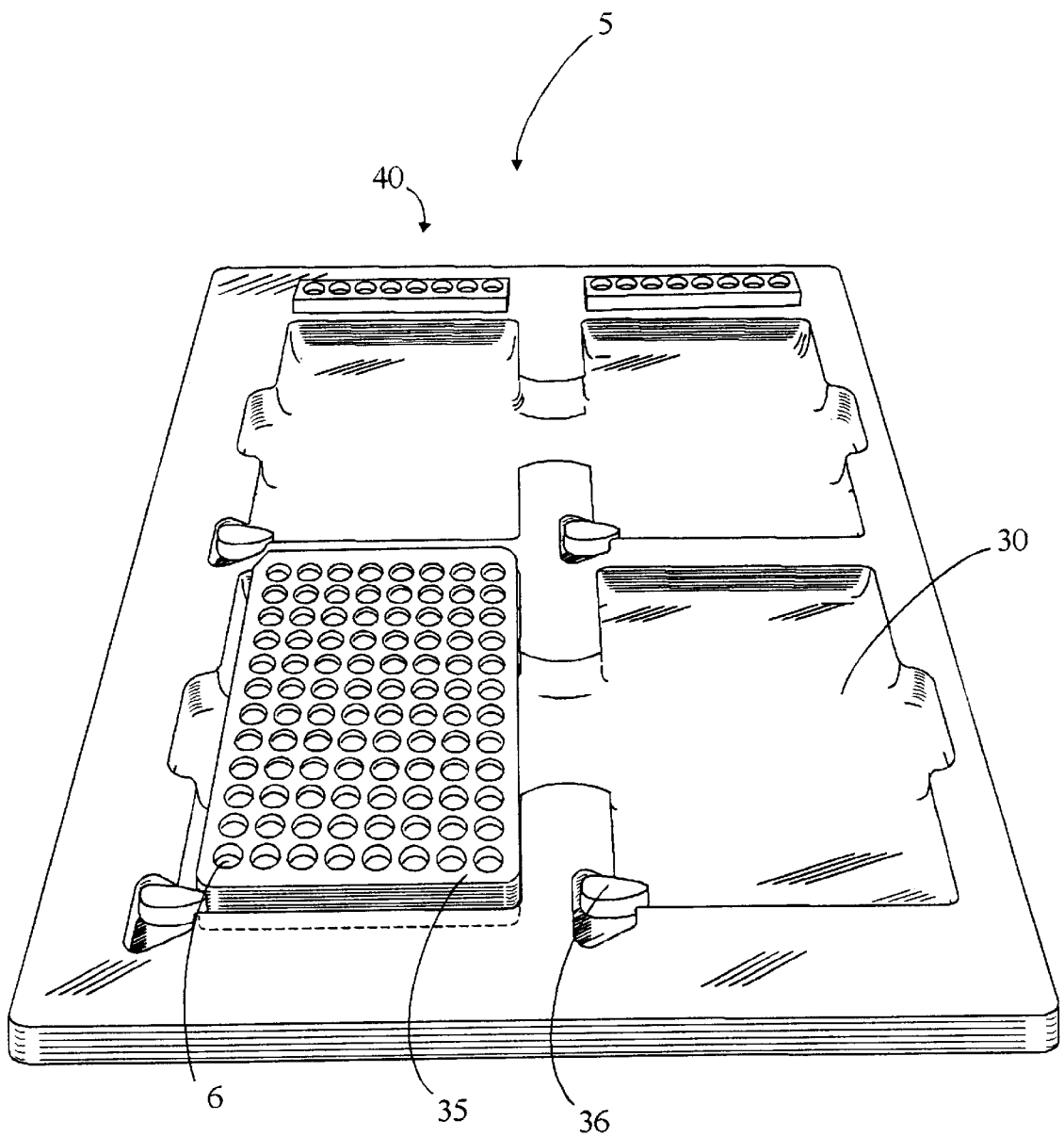
FIG. 2 shows a preferred work surface according to the present invention.

FIG. 2 shows a preferred work surface 5 according to the present invention. The work surface includes four tray recesses 30 for accommodating four replaceable sample trays 35, e.g., disposable 96-well microtiter plates. Each tray recess is associated with a tray locking mechanism 36 for rigidly and precisely locating the sample tray in the recess. Preferably, the locking mechanism is a spring and latch mechanism. In addition to the sample trays, the work surface shown in FIG. 2 includes a plurality of standard wells 40 for containing internal and or external standard materials. In the case of automated nucleic acid analysis, the standards may be molecular weight standards or spectral calibration standards.

B. Sample Transfer Device

The programmable sample transfer device of the present invention serves to transport samples from a work surface coordinate, e.g., a sample well, to a loading well such that there is no fixed correspondence between a particular work surface coordinate and a particular loading well. Rather, the correspondence between the work surface coordinate and the loading well is controlled by a program controlling the sample transfer device. In an important feature of the invention, the correspondence between a work surface coordinate and a loading well may be changed during the course of a multi-injection analysis. Thus, if a particular loading well, or its associated capillary tube, becomes inoperative, the sample transfer device can bypass that loading well and deposit the sample into an operative loading well. This feature of the present invention is in contrast with existing multi-channel capillary electrophoresis devices which embody a fixed relationship between a particular sample well and capillary tube.

As shown in FIG. 1, a preferred programmable sample transfer device 25 according to the present invention comprises (1) a multi-axis robot 45 including a robot arm 50, and (2) a pipette head 55 including one or more pipettes 56 located on the robot arm.

1. Multi-Axis Robot. The multi-axis robot of the preferred embodiment may be any conventional programmable robot capable of defined motion along two or more axes. For example, the robot may be a three-axis robot having three linear axes, e.g., x, y and z axes, or a combination of linear and rotary axes, e.g., r, θ and ω axes. Preferably, the multi-axis robot is a three-axis robot having three linear axis.

Generally, the multi-axis robot of the preferred embodiment includes an arm 50 for supporting elements to be robotically manipulated, and a linear or rotary actuator to provide motive power for propelling the arm along each axis. The actuator generally comprises a motor for providing a motive power, and a transmission for delivering the power with a desired torque and velocity. Exemplary motors include AC or DC electric motors, pneumatic or hydraulic driving mechanisms. Exemplary transmissions include but are not limited to belt drive, rack and pinion, and ball screw transmissions. Preferably, the transmission is a belt drive transmission. In addition, the multi-axis robot generally includes a linear and/or rotary bearing guide to control the direction of motion along each linear and/or rotary axis, respectively. Such bearing guides may include ball bearings, air bearings or journal bearings.

Preferably, the multi-axis robot further includes a positional feedback mechanism for monitoring the location of the robot arm 50 and the pipettes 56. A positional feedback mechanism of the preferred embodiment generally comprises three elements for monitoring three levels of positional feedback: (1) a positional encoder, (2) one or more limit switches and (3) a tip-sensor. The positional encoder serves to measure the position of the arm during travel within the robot's motion envelope, i.e., between the limit switches. Preferably, the resolution of the encoder is to within 0.025 mm. An exemplary encoder includes an etched glass scale mechanically coupled to the robot arm and optically coupled to an optical monitor which monitors a location on the glass scale, e.g., a LED and photodiode optical monitor. The limit switches serve to define the limits of the robot's motion envelope, e.g., using a flag mechanically coupled to the robot arm, and an LED and a beam sensor located at the periphery of the robot's motion envelope.

In an important feature of the three-axis robot of the preferred embodiment, a tip sensor serves to provide a precise location of an inlet 135 of pipettes 56. The tip sensor is important because it allows the robot to compensate for non-idealities in the location of the pipette's inlet end with respect to the robot arm, e.g., non-idealities caused by a bent pipette or the mispositioning of any of the elements addressed by the pipette, e.g., mispositioning of the loading bar or sample wells. Preferably, the tip sensor should be repeatable to within about ±0.025 mm.

A variety of mechanisms may be employed to implement the tip sensor, e.g., electrical mechanisms, e.g., a capacitive sensor or a conductance sensor, or optical mechanisms, e.g., a video system and image analysis software. Preferably, the tip sensor uses a capacitive sensor wherein a voltage is placed across the pipette tip such that when the pipette approaches or contacts a conductive surface, or "landing pad," the capacitance of an electrical circuit including the pipette is changed, thereby indicating contact or close proximity of the pipette tip with the landing pad. One or more landing pads are located at strategic locations within the robot's motion envelope to provide benchmarks suitable for locating the pipettes with respect to key components of the system.

2. Pipette Head. The pipette head of the sample transfer device serves to collect a sample from the work surface, contain the sample during transfer between the work surface and a loading well, and dispense the sample into a loading well. The pipette head should be capable of collecting micro-liter volumes of sample in a controlled and reproducible manner, e.g., 2.5 $\mu l \pm 15\%$ by volume.

Figure 3:
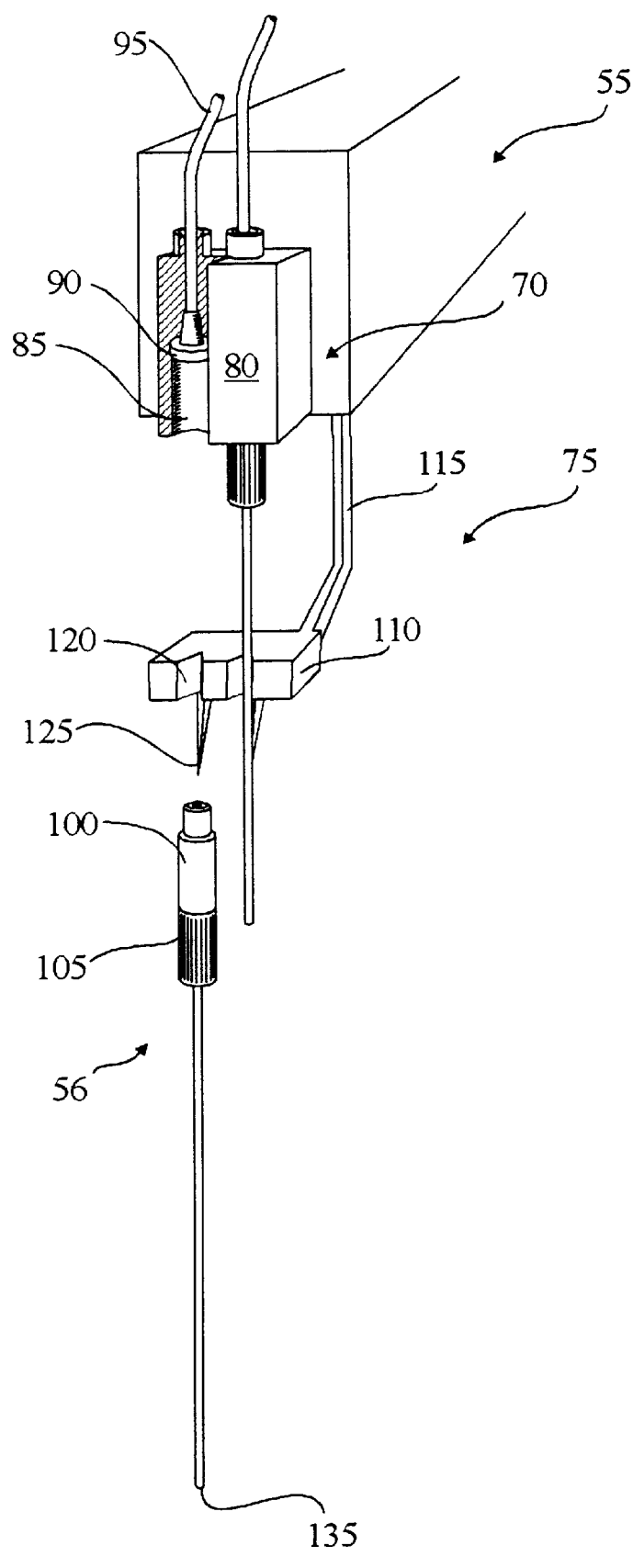
FIG. 3 shows a preferred pipette head according to the present invention.

A preferred pipette head of the present invention is shown in FIG. 3. As indicated in the figure, the pipette head 55 includes (1) pipettes 56, (2) tip housing 70, and tip (3) straightener 75. The pipette head may be in fluid communication with associated fluidics not shown in the figure, e.g., vacuum pumps, fluid passages and fluid pumps.

Generally, the pipettes of the invention may be any pipette capable of containing a micro-liter volume of a sample, preferably between about 0.1 and 10 $\mu l$ of a fluid sample. While the pipette may be any shape suitable for a particular application, preferably the pipette has a circular cross-section.

The material used to fabricate the pipette will depend upon the requirements of a particular application. Factors to be considered include wetability, rigidity and conductivity. Where the sample is a liquid, the wetability of the pipette should be such that sample may be introduced into the pipette in a controlled and reproducible manner. When the pipettes are passively loaded with sample using capillary action, generally the pipette should be wetable by the sample material. It is preferable that the pipette be rigid in order to facilitate location of the inlet end of the pipette with respect to the robot arm. Finally, where an electrical measurement is used in the tip sensor, the pipette should be electrically conductive. Preferred pipette materials include but are not limited to stainless steel, platinum and gold coated materials, glass, fused silica, and plastic or plastic coated materials, e.g., stainless steel coated with a parylene.

While FIG. 3 shows a pipette head having two pipettes, any number of pipettes may used. However, the following trade-off must be considered. As more pipettes are used; the speed with which the device can transport multiple samples from the work surface to the loading wells is increased. However, the problem of accurate tip location is aggravated as the number of pipettes is increased. Preferably, the number of pipettes ranges from one to 20 pipettes, and more preferably, between about two and eight pipettes.

The tip housing 70 of the preferred pipette head of FIG. 3 serves to provide a mechanical connection between the pipettes and the robot arm, and a fluid connection between the pipettes and any fluidics associated with the pipettes. The tip housing 70 comprises a body 80, a tip insert 85, a ferrule 90, and a fluid channel 95. The tip insert 85 provides a means to align the pipette with respect to the ferrule 90 such that a user may easily replace the pipette. The tip insert is adapted to receive a mounting portion 100 of the pipette 56 such that the pipette is securely held in the insert. Preferably, to further facilitate the replacement of a pipette, the pipette mounting portion 100 has a grippable holding portion 105. The ferrule 90, in combination with the tip housing, serves to provide a fluid-tight seal between the pipette 56 and the fluid channel 95. Fluid channel 95 may be in fluid communication with associated fluidics useful for effecting the collection and/or ejection of a sample into and/or out of the pipette. For example, to facilitate sample collection, the fluid channel 95 may be connected to a vacuum source for aspirating a sample into the pipette. Conversely, to facilitate sample ejection of the sample out of the pipette, the fluid channel 95 may be connected to a pressure source. Such fluid connections may be mediated by one or more single- or multi-port valves, pressure sources, and/or vacuum sources.

In an important feature of the pipette head of the preferred embodiment, the pipette head includes a tip straightener mechanism 75. The tip straightener serves to establish, or reestablish, a defined spacing between two or more pipettes of a multi-pipette sample handling system. Thus, if the location of a first pipette is established using a tip sensor, e.g., a capacitive tip sensor, the location of a other pipette may be established based on the location of the first pipette if a defined spacing between the pipettes can be established.

FIG. 3 shows a preferred tip straightener according to a preferred embodiment as applied to a two-pipette pipette head. The tip straightener 75 comprises (1) a tip guide 110, (2) an arm 115, and (3) a linear actuator (not shown). The tip guide 110 serves to define a separation distance between the two pipettes. The separation distance may be any distance required in a particular application, however, to be compatible with standard titer plate formats, preferably the separation distance is 9 mm or an integral fraction thereof, e.g., ½ mm, ⅓ mm, ¼ mm, etc. The pipettes are seated in V-grooves 120 formed in the tip guide. Alternatively, the pipettes may pass through holes through the tip guide. Optionally, the tip guide 110 includes one or more puncture features 125. These puncture features serve to puncture a sealing material covering sample wells, e.g., a Parafilm™ sheet covering a 96-well micro-titer plate. The linear actuator may be any actuator that effects the reciprocal motion of the tip guide 110. Preferably, the tip straightener mechanism includes a positional feedback system.

Figure 6:
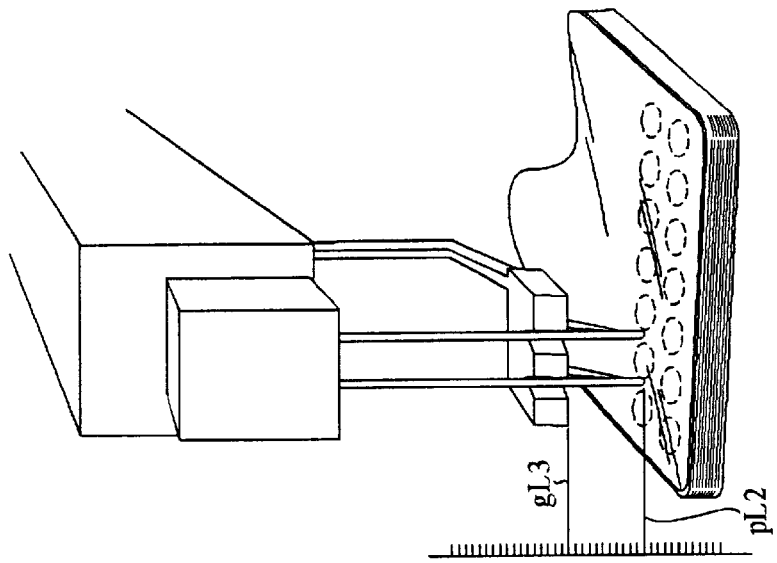
FIG. 6 shows a preferred tip straightner according to the present invention in a intermediate position.
Figure 5:
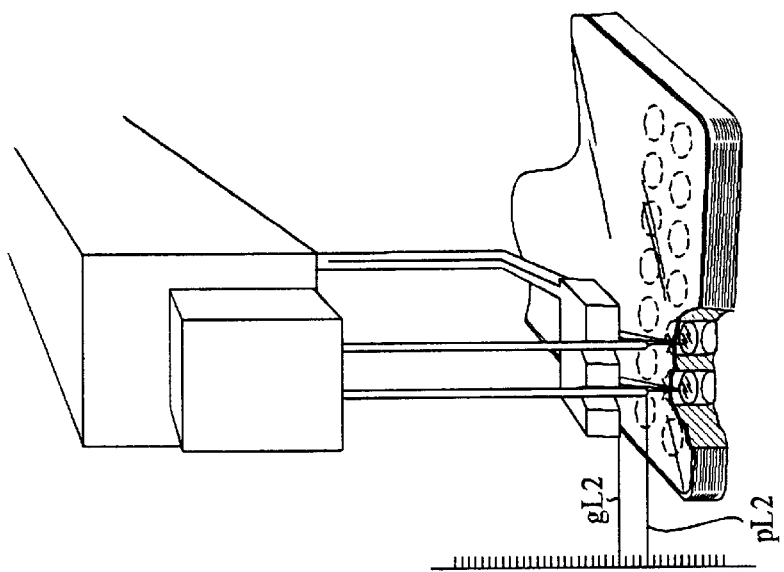
FIG. 5 shows a preferred tip straightner according to the present invention in a fully extended position.
Figure 4:
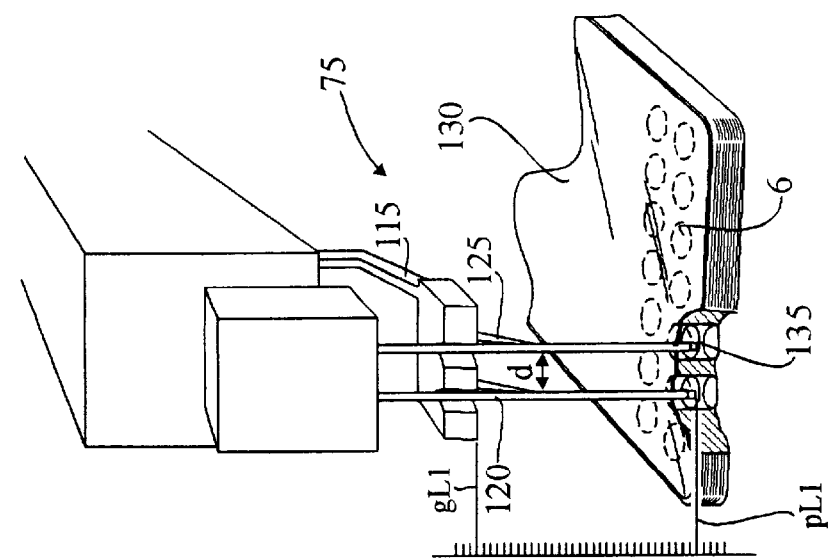
FIG. 4 shows a preferred tip straightner according to the present invention in an fully retracted position.

FIGS. 4–6 shows the tip straightener in operation. FIG. 5 shows the tip straightner in a fully extended position in which the puncture features are puncturing a cover film 130 covering the sample wells 6. In this extended position, the puncture features extend beyond the tips of the pipettes to puncture the cover film. FIG. 4 shows the tip straightner in a fully retracted position. In this position, the tip straightener is separated from the pipette inlets 135 to a maximum extent so as to allow the pipettes to access deep reservoirs or troughs without interference from the tip straightener. FIG. 6 shows the tip straightner in an intermediate position. In this position, the tip straightner provides a rigid spacing between the inlets of the pipettes while at the same time providing sufficient distance between the pipette inlets and the tip guide 110 to allow the pipette inlets 135 to access shallow containment wells. This is the position of the tip straightener when the pipettes are located in a sample well or a loading well.

C. Sample Loading Assembly

The sample loading assembly of the present invention provides a means for ringing a sample in contact with an inlet of a capillary tube such that the sample can be lectrokinetically or hydrodynamically introduced into the capillary tube. Moreover, the ample loading assembly allows for the handling of small volumes of sample, e.g., between 0.1 and 5 $\mu$l volume, and does not require any relative motion between loading wells and the capillary tubes. In addition, the sample loading assembly may provide an electrode and electrode reservoir capable of performing electrokinetic injection of multiple samples located in multiple loading wells. Optionally, the sample loading assembly further provides a means for washing the exterior surface of a pipette associated with the sample transfer device 25. The capillary tubes 21 within which electrophoresis is performed are fixedly located in the loading wells during operation of the system.

As shown in FIG. 7, a preferred loading assembly according to the present invention comprises (1) a loading bar 150 including multiple loading wells 20, (2) a loading block 155 for supporting the loading bar, and (3) one or more block supports 160 for supporting the loading block.

Figure 8:
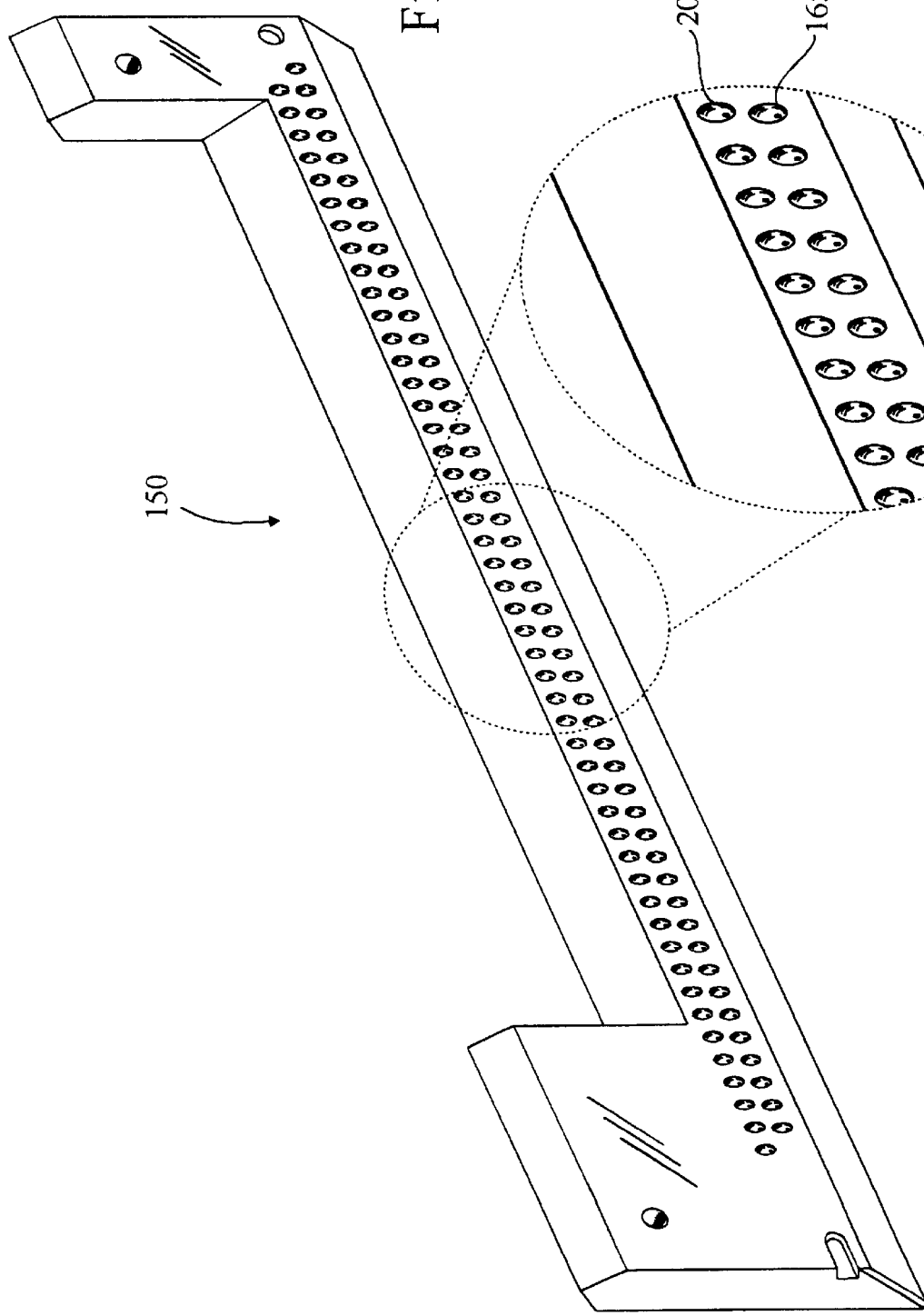
FIG. 8 shows a preferred loading bar according to the present invention.
Figure 9:
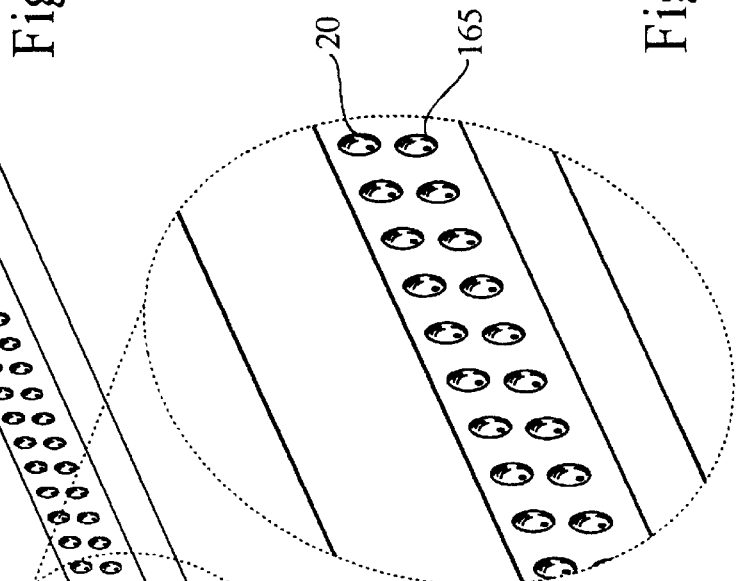
FIG. 9 shows an expanded view of the loading bar of FIG. 8.
Figure 10:
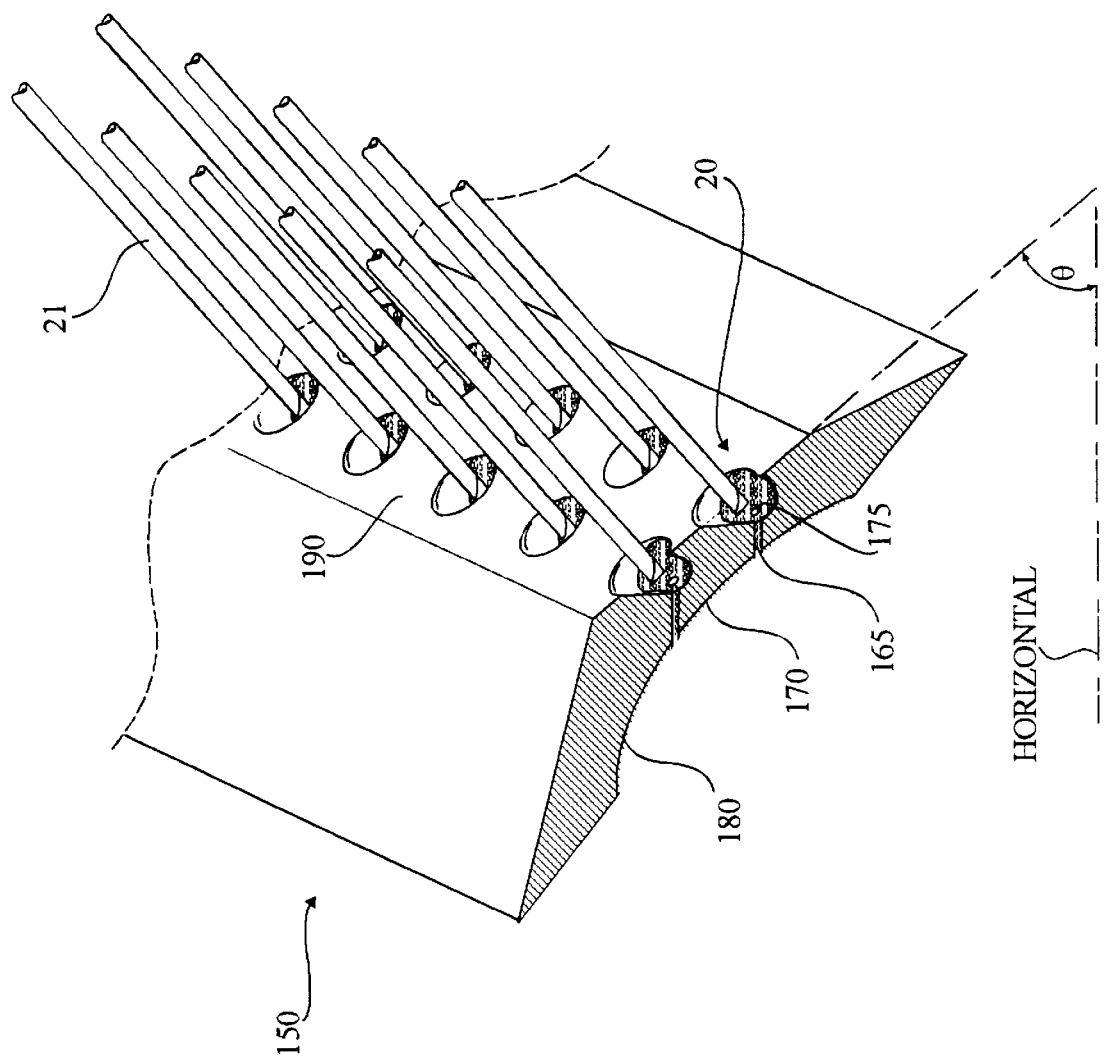
FIG. 10 shows an expanded cross-sectional view of the loading bar of FIG. 8 including two loading wells and their associated fluid passages and capillary tubes.

1. Loading Bar. According to the preferred embodiment, the loading bar 150 includes one or more loading wells 20, and may serve as an electrode during electrophoresis. A detailed view of a preferred loading bar is shown in FIGS. 8–10.

The loading wells 20 located in the loading bar 150 include fluid passages 165 for introducing fluids into the loading wells, e.g., wash solvents for washing the loading wells between samples or electrophoresis buffer, and for removing fluids from the loading well, e.g., drying the loading wells after washing with wash solvents or removing residual sample after an injection step. An expanded cross-sectional view of two loading wells 20 and their associated fluid ports 165 and capillary tubes 21 is shown in FIG. 10.

The fluid passages 165 preferably have relatively small diameters to reduce unwanted leakage of material out of the loading well 20, and to cause a high flow resistance through the fluid port. This high flow resistance is important to ensure a uniform pressure drop across each of the fluid passages. This uniform pressure drop is required to avoid uneven flow of fluids through the ports. That is, when applying a vacuum to a rear surface 170 of the loading bar, if the flow resistance across each of the fluid passages is too small, it is difficult to maintain a constant flow through all of the fluid ports, particularly when some loading wells contain fluid and others do not. Preferably, the fluid passages have an internal diameter from about 0.005 to about 0.02 inches. An inlet 175 to the fluid passage is preferably located at or near the bottom of the loading well to facilitate complete draining of the loading well. In addition, preferably the fluid passage is substantially horizontal to reduce unwanted draining from the loading well and to reduce jetting of fluid from the loading well when introducing fluid into the loading well. To facilitate fabrication of the fluid passages 165, preferably the path length of the passages is small, e.g., less than about 5 mm. To reduce the path length of the fluid passages, the rear surface of the loading bar preferably includes a concave portion 180 in the vicinity of the fluid ports. The fluid passages can be fabricated using any one of a number of well known process, the preferred process depending upon the size of the passage and the material used to form the loading bar. For a metallic loading bar, e.g., 316 stainless steel, preferred passage-forming techniques include electrical discharge machining (EDM), mechanical micro-drilling and laser drilling.

The number of loading wells 20 will generally correspond to the number of capillaries 21 used in the electrophoresis system. However, in some cases, extra loading wells are required to create a uniform pressure distribution across the fluid passages 165, and to ensure that all fluid is removed from the active wells.

As shown in FIG. 10, a front face 190 of the loading bar 150 is preferably tilted at an angle $\theta$ with respect to horizontal. This tilt angle allows the capillary tubes 21, which are in a horizontal orientation along most of their length, to enter the loading wells without having to bend around a sharp corner. Thus, the separation will not be compromised by a "race-track" effect in which electrophoresis zones are broadened due to path-length differences between inner and outer edges of a bend. However, if the face of the loading well is tilted at too large an angle, material will not be effectively contained in the loading well. Alternatively, if the face of the loading well is tilted at too small an angle, fluid will tend to pool in the well making it more difficult to dry the wells. Preferred tilt angles $\theta$ range between about 20° and 70°, with tilt angles of about 45° being most preferred.

The pitch (or inter-well spacing) of the loading wells 20 may be any pitch consistent with a given application. However, generally it is preferred to reduce the pitch to a minimum in order to accommodate a maximum number of wells in a given area. Because there is no need for an operator to address the loading wells, and because there is no relative movement between the loading wells and the capillaries, the pitch can be minimized. As was the case for the spacing of the pipettes 56 of the sample transfer device, preferably the pitch of the loading wells is an integral fraction of 9 mm. A particularly preferred pitch is 2.25 mm. To further increase the density of loading wells, a multi-tier arrangement may be used. For example, the loading wells 20 in FIG. 10 are arranged in a two-tier arrangement, thus providing an effective pitch of 1.125 mm.

The loading bar should be made from a material that allows fabrication of the loading wells 20 and fluid passages 165, is chemically compatible with the samples and other materials to which the loading bar will be exposed, e.g., D.I. water, aqueous polymer solutions, acid, organic solvents, and is optionally electrically conductive. Exemplary materials include but are not limited to stainless steel, platinum, gold, ceramic, glass, and silicon. A particularly preferred material for fabricating the loading bar is 316 stainless steel. Many times it is desirable to treat the surface of the loading bar in order to optimize its surface properties, e.g., the surface may be passivated to reduce the amount of ionic species present, electropolished to remove surface contaminants, or electroplated, e.g., deposition of gold or platinum onto the surface of the loading bar.

In an important feature of the present invention, the loading bar 150 may serve as an electrode. By using the loading bar as an electrode, electrokinetic injection of a sample from a loading well 20 into a capillary tube 21 is facilitated because there is no need to place a separate electrode in the loading well. In addition, a more uniform electric field is produced in the loading well during electrokinetic injection because the electrode effectively surrounds the sample.

2. Loading Block.

The loading block serves several important functions in the sample handling system of the present invention. Specifically, these functions include (1) mechanically supporting the loading bar, (2) conducting fluids into and out of the loading bar, (3) providing an electrical connection between the loading bar and a voltage source or ground, (4) furnishing an electrode reservoir for containing an electrolyte, e.g., an electrophoresis buffer, and (5) providing electrical isolation between the loading assembly and the other elements of the capillary electrophoresis system. Optionally, the loading block provides a reservoir for containing a wash solution for washing the exterior surface of the pipette tips of the sample transfer device.

Figure 11:
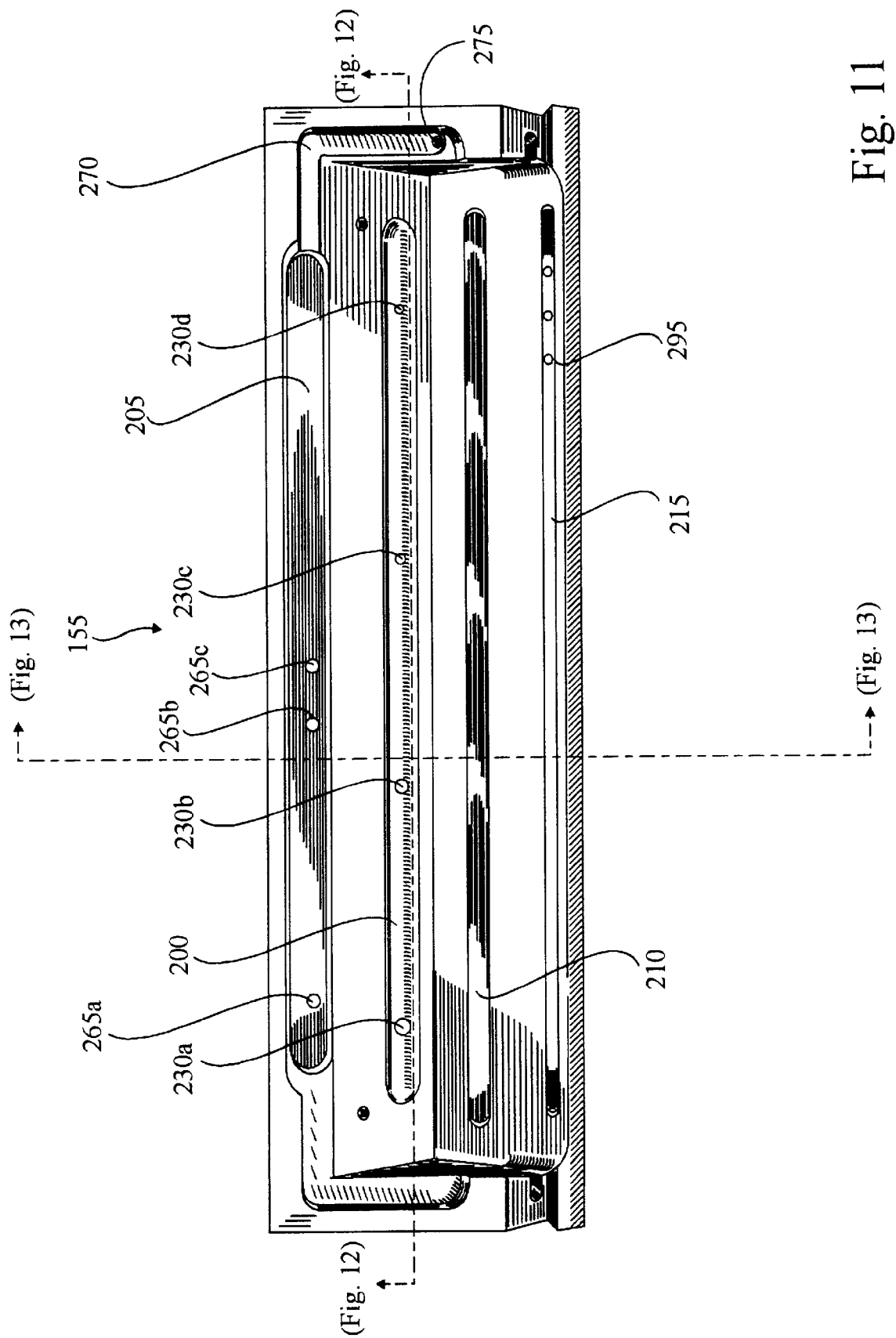
FIG. 11 shows a top view of a preferred loading block according to the present invention.
Figure 13:
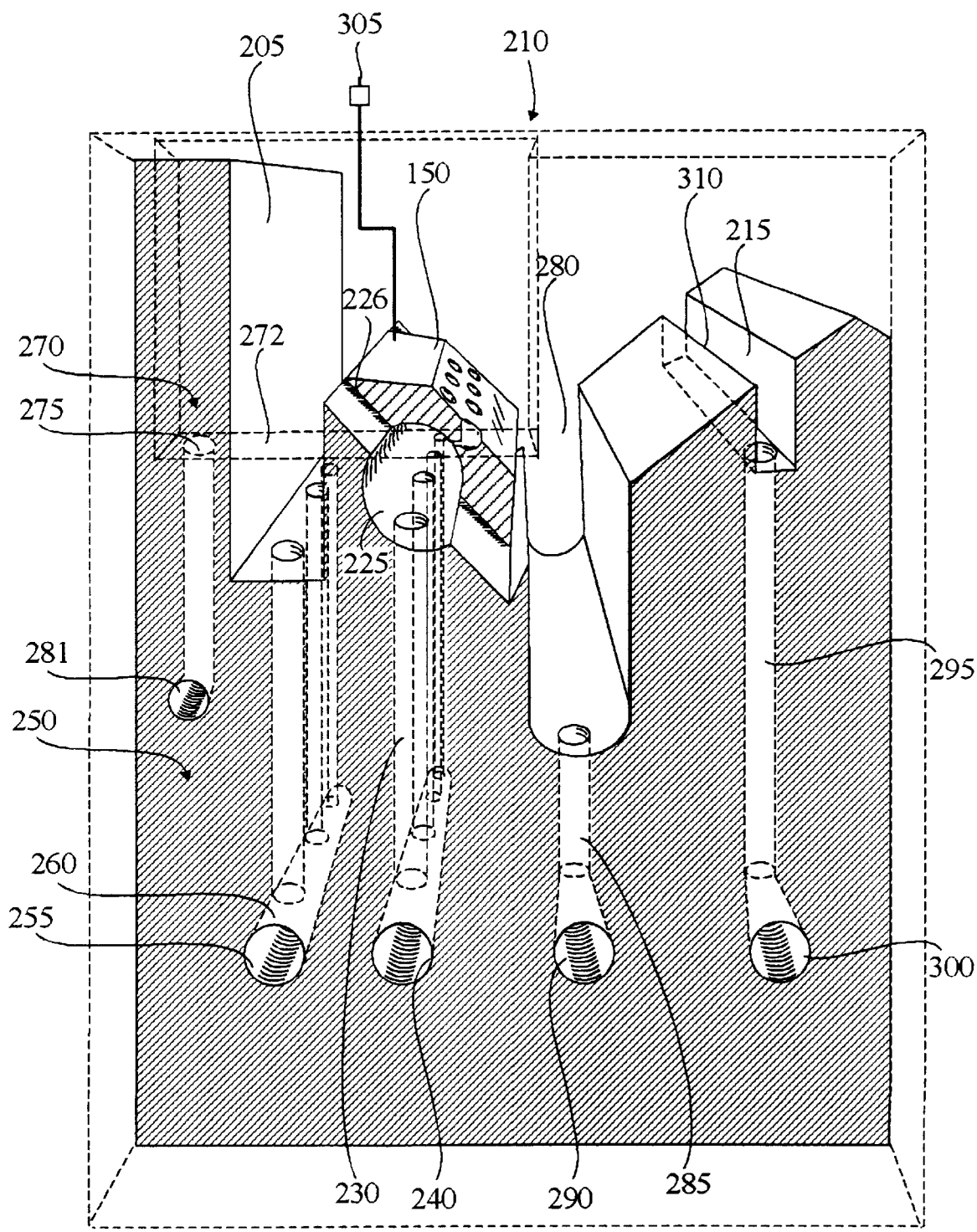
FIG. 13 shows a cross-sectional view of the loading block of FIG. 11.

FIG. 11 shows a top view of a preferred loading block 155 of the present invention. As indicated in the figure, the preferred loading block 155 includes main manifold 200, tip-wash trough 205, electrode reservoir 210, and electrode reservoir overflow gutter 215. FIG. 13 shows a cross-sectional view of the loading block 155 of FIG. 11 depicting various troughs and fluid passages that will be referred to below, and the positioning of the loading bar 150 with respect to the main manifold 200 of the loading block 155.

Figure 12:
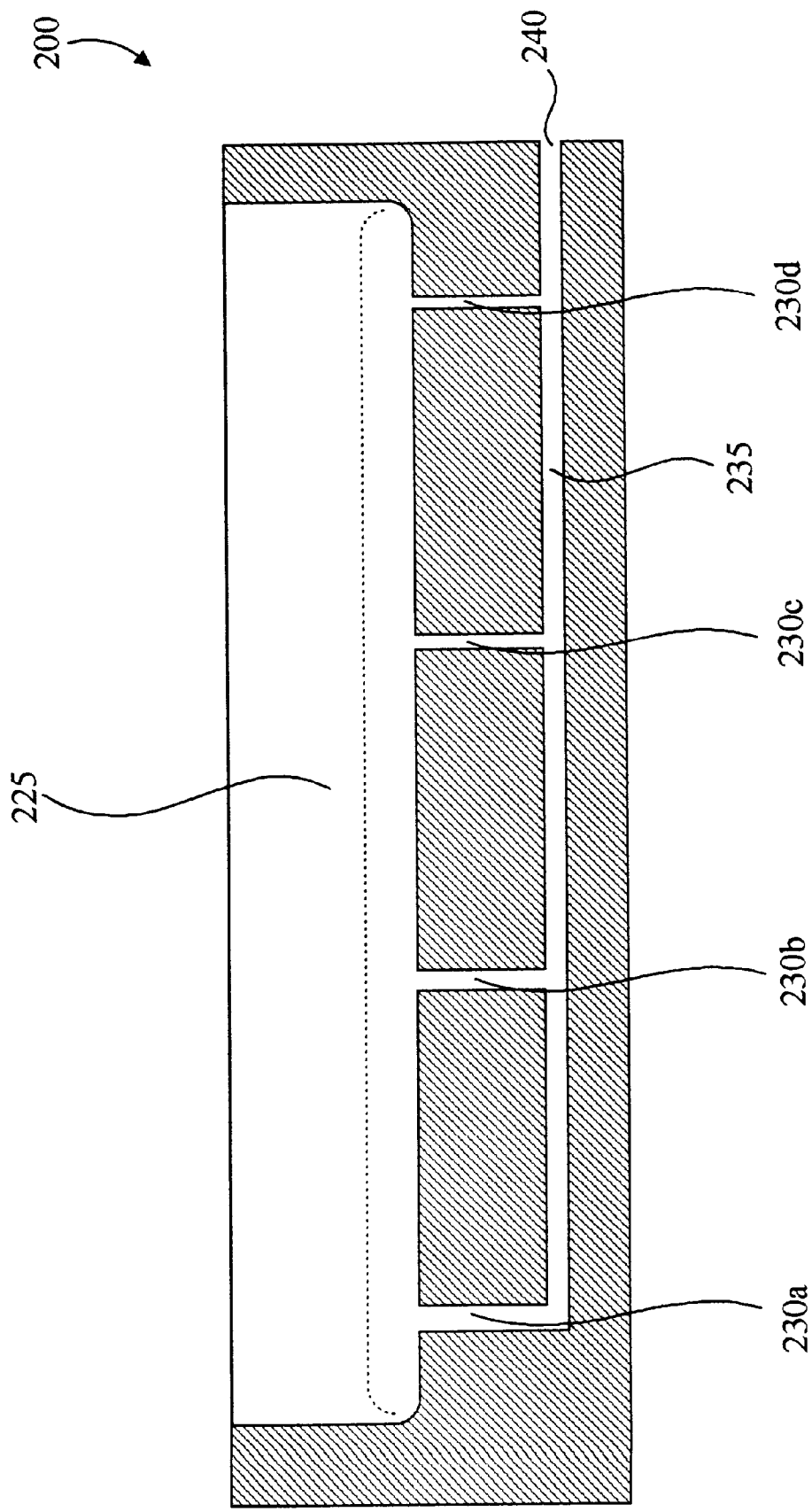
FIG. 12 shows a cross-sectional view of a preferred main manifold according to the present invention.

The main manifold 200 provides a means for conducting fluids into and out of each of the loading wells 20 of the loading bar 150. As shown in the cross-sectional view depicted in FIG. 12, the main manifold comprises a manifold recess 225, manifold passages 230, common passage 235, and main manifold inlet/outlet port 240.

As best seen in FIG. 13, the loading bar 150 sits on top of the manifold recess 225 such that a chamber is formed by the manifold recess and the loading bar. Preferably, a gasket 226, e.g., a hydrophobic gaskit, is disposed between the manifold recess and the and loading bar to ensure a fluid-tight seal.

The main manifold 200 further includes manifold passages 230 for providing fluid communication between the main passage 235 and the manifold recess 225. In an important feature of the invention, the diameter of each of the manifold passages 230 is selected to cause an even flow rate of fluid or vacuum through each of the manifold passages irrespective of its proximity to the main manifold inlet/outlet port 240. Specifically, manifold passages that are farther away from the manifold inlet/outlet port have a larger diameter than manifold passages that are closer to the manifold inlet/outlet port. Thus, the diameter of manifold passage 230a is greater than that of manifold passage 230b, which is greater than that of manifold passage 230c, which is greater than that of manifold passage 230d.

The main passage 235 of the main manifold 200 serves to provide a common flow path between the manifold passages 230 and the main manifold inlet/outlet port 240. The main manifold inlet/outlet port 240 serves to provide fluid communication between the main manifold 200 and sources of fluids and/or vacuum, e.g., a liquid diaphragm pump and a vacuum pump.

The tip-wash trough 205 of the loading block 155 serves to contain a tip-wash liquid, e.g., D.I. water, that may be used to wash the exterior surface of the pipette tips at various stages of a sample transfer operation. Preferably, the tip-wash trough 205 is approximately the same length as the loading bar 150 in order to minimize the travel distance between the loading wells 20 and the tip-wash trough. Referring to FIG. 13, liquid enters the tip-wash trough through tip wash manifold 250, such manifold comprising tip wash inlet/outlet port 255, tip wash main passage 260, and tip wash manifold passages 265. Referring to FIG. 11, the tip-wash trough further includes an overflow gutter 270 for maintaining a liquid level in the tip-wash trough at or below a maximum level. Liquid exits the overflow gutter 270 through gutter passage 275 and gutter outlet port 281. In a preferred embodiment of the tip-wash trough 205, the trough includes a set of tip wash manifold passages 265b and 265c whose spacing is the same as that of the pipettes 56 of the sample transfer device 25. When the pipettes are inserted into these passages, fluid can be pumped through the passages to effect an agitation thereby enhancing the efficacy of the tip wash.

The electrode reservoir 210 serves to contain an electrolyte in electrical communication with an electrode and loading wells 20 for supplying ionic species required to perform electrophoresis. The electrode reservoir includes main trough 280, and overflow trough 215. The main trough 280 includes outlet passage 285 and outlet port 290. The overflow trough 215 includes outlet passage 295 and outlet port 300. Fluid enters the electrode reservoir through the fluid passages 165 of the loading bar 150. The maximum fluid level in the electrode reservoir is determined by a height of front edge 310 of the overflow trough 215. Fluid is removed from the main trough 280 through drain passage 285 and outlet port 290.

When the loading bar 150 serves as an electrode, the loading bar is connected to a voltage source or ground through electrical connector 305.

The location of the loading block in the capillary electrophoresis system of the invention may be adjusted based on the length of the capillary tubes employed in a given analysis. Thus, when shorter capillaries are used, prior to performing electrophoresis, the loading block may be positioned in a block support location closer to a detector.

3. Associated Fluidics.

Figure 14:
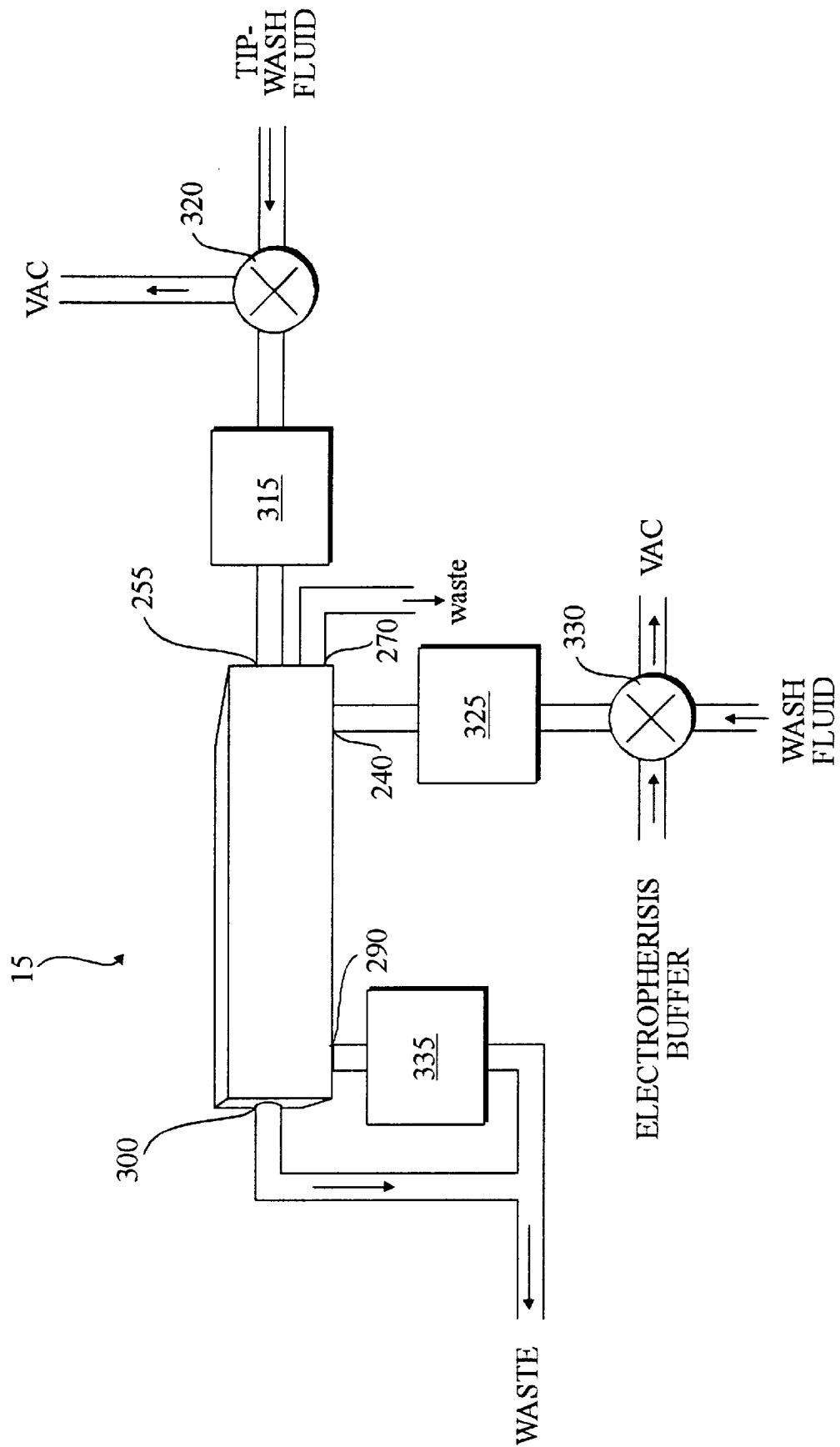
FIG. 14 shows a schematic plumbing diagram of a preferred system used to conduct of fluids through the sample loading assembly.

FIG. 14 shows a schematic plumbing diagram indicating fluidics used to control the flow of fluids to and from the sample loading assembly 15. First solenoid valve 315 is in fluid connection with the tip-wash inlet/outlet port 255 and controls the flow of fluid into and out of the tip-wash trough 205. First solenoid valve 315 is in fluid connection with first multi-port selector valve 320 for selecting between a vacuum and a tip-wash fluid. Second solenoid valve 325 is in fluid connection with the main manifold inlet/outlet port 240 and controls the flow of fluid into and out of the main manifold 200. Second solenoid valve 325 is also in fluid connection with second multi-port selector valve 330 for selecting between a vacuum, a wash fluid and an electrophoresis buffer. Third solenoid valve 335 is in fluid connection with the electrode reservoir outlet port 290 and controls the flow of fluid out of the main trough 280 of the electrode reservoir 210. The output of the third solenoid valve 335 simply drains to waste. The outlet port 300 of the electrode reservoir overflow trough 215, and the outlet 281 of the overflow gutter 270 both drain to waste.

III. ADDITIONAL FEATURES

The electrophoresis device of the invention also includes other elements required to conduct a capillary electrophoresis process, e.g., electrodes in electrical communication with the capillary outlets, a power supply connected to the electrodes for creating an electrical field within the lumen of the capillaries, a detection system for detecting samples subsequent to electrophoresis, a temperature controller for controlling the temperature of the device, and a computer to control the functions of the device and for data collection and analysis. Details of these and other common features of an operable capillary electrophoresis device may be found in any number of available publications, e.g., *Capillary Electrophoresis Theory and Practice*, Grossman and Colburn, eds., Academic Press (1992). A particularly preferred sheath-flow detection cell and replaceable capillary array are described in co-pending U.S. patent application Ser. No. 09/151,928, filed on or about Sep. 11, 1998, titled "Multi-Channel Capillary Electrophoresis Device Including Sheath-Flow Cuvette and Replaceable Capillary Array" by Nordman et al..

IV. OPERATION OF INPUT SAMPLE HANDLING SYSTEM

The preferred embodiment of the sample handling system described above operates as follows.

First, loading wells 20 are flushed with a wash fluid, e.g., D.I. water. The flush is performed by flowing a wash fluid into main manifold 200 through the main manifold inlet/outlet port 240, through common passage 235, through manifold passages 230, into manifold recess 225, and out fluid passages 165. The wash fluid then overflows from the loading wells 20, drains into the main trough 280 of the electrode reservoir 210, and through outlet passage 285 and outlet port 290. Thus, referring to the diagram of FIG. 14, during the flush step solenoid valves 325 and 335 are open, and multi-port selector valve 330 is open to a wash fluid.

Next loading wells 20 are dried in preparation for loading of the samples. It is important to dry the loading wells prior to loading the wells with samples to avoid dilution of the samples with wash fluid and/or cross-contamination between different samples. To effect the drying of the loading wells, a vacuum is applied to main manifold 200, thereby pulling any liquid located in the loading wells 20 out of the loading wells through fluid passages 165. Thus, referring to FIG. 14, during the well drying step, solenoid valve 325 is open and multi-port selector valve 330 is open to vacuum.

In an important step of the process of the preferred embodiment, once the loading wells 20 have been dried, the valves and fluid lines leading to or from the electrode reservoir 210 and the main manifold 200 is dried. This is done to ensure that when voltage is applied to an electrode in the electrode reservoir during sample injection, none of the resulting current escapes through the valves or fluid lines associated with the electrode reservoir or main manifold. The valves and fluid lines are dried by opening multi-port selector valves 320 and 330, and venting the fluid lines between the solenoid valves and the multi-port selector valves to atmosphere (vents not shown).

Next tip wash trough 205 is filled with a tip wash fluid. Fluid enters the tip wash trough 205 through tip wash inlet/outlet port 255 and tip wash manifold passages 265. The level of fluid in the tip wash trough 205 is governed by the height of a front face 272 of gutter 270. When the fluid level in the trough reaches the height of the front face of the gutter, liquid drains from the trough into the gutter, and out of the gutter through gutter outlet passage 275 and gutter outlet port 281. Thus, referring to FIG. 14, during the tip wash trough filling step, solenoid valve 315 is open, and multi-port selector valve 320 is open to tip wash fluid.

Next, samples are transferred from the work surface 5 to the loading wells 20 by the sample transfer device 25. To effect the sample transfer, pipettes 56 are immersed in samples located in selected sample wells 36, and samples are aspirated into the pipettes by application of a vacuum to the pipettes through fluid channels 95. The sample transfer device 25 then moves the pipettes to selected loading wells 20, and the samples are ejected from the pipettes 56 by pressurizing fluid channels 95. In a preferred transfer, approximately 2.5 $\mu$l of material is deposited in each loading well.

Once the pipettes 56 have ejected the samples into the loading wells 20, the pipettes may be passed through the tip wash trough 205 to remove any sample that may remain on the external surface of the pipettes. Removal of such sample is desirable to reduce the likelihood of cross-contamination between samples. In an important feature of the preferred embodiment, the pipettes are immersed in the tip wash trough 205 while the pipettes are moving from one end of the trough to the other. Immersing the pipettes while they are moving provides at least two advantages over static immersion. First, because the robot arm 50 of the sample transfer device does not have to decelerate during the tip wash step, the step is faster. Second, the relative motion between the pipettes 56 and the tip wash fluid results in a more through washing. Also, the inside of the pipettes may be washed by pumping a wash fluid through the pipette through fluid channel 95.

The steps of transferring sample from the work surface 5 to the loading wells 20, and washing the pipettes between sample transfers, are repeated until all the samples that are to be analyzed have been transferred.

Once the loading wells 20 have been prepared to receive samples, and the samples have been transferred from the work surface 5 to the loading wells, then the samples are electrokinetically injected into the capillaries 21. Such electrokinetic injection is performed using conventional techniques by imposing an electrical potential difference between the sample located in the loading well and the lumen of the capillary tube. In the preferred embodiment, this is achieved by employing the loading bar 150 as one of two electrodes used to effect the electrical potential difference. While in the preferred embodiment, sample are injected electrokinetically, hydrodynamic injection may also be used, i.e., by applying a pressure difference across the capillary tubes.

After the samples have been injected into the capillaries 21, any sample material remaining in the loading wells is flushed from the loading wells 20 by flowing a wash solution through the loading wells as described above with respect to the first loading well flushing step. However, this flushing step must not be so violent as to disturb the samples that have been injected into the capillary tubes. Thus, a lower velocity flow may be desirable for this loading well flush relative to the first loading well flush.

Next, prior to beginning the electrophoresis, the electrode reservoir 210 is filled with an electrolyte, e.g., an electrophoresis buffer. The electrode reservoir is filled by flowing the buffer into the main manifold 200 and out the fluid passages 165 until the electrode reservoir 210 is filled to the level of the front edge 310 of the overflow trough 215. Fluid entering the overflow trough 215 then exits the trough through outlet passage 295 and outlet port 300. Thus, referring to the diagram of FIG. 14, during the electrode reservoir filling step solenoid valve 325 is open, and multiport selector valve 330 is open to electrophoresis buffer. When the electrode reservoir 210 is filled to the level of the front edge 310 of the overflow trough 215, the loading bar 150 will be largely submerged in electrolyte.

Before conducting the electrophoretic separation, the fluid lines serving the electrode reservoir 210 and main manifold 200 are again dried as described above to ensure the electrical isolation of the fluid delivery system from the electrophoretic voltage. As before, this is done to ensure that when voltage is applied to the loading bar 150 during electrophoresis, none of the resulting current escapes through the fluid lines associated with the electrode reservoir 210 or main manifold 200.

All publications and patent applications referred to herein are hereby incorporated by reference to the same extent as if each individual publication or patent application was specifically and individually indicated to be incorporated by reference.

Although only a few embodiments have been described in detail above, those having ordinary skill in the electrophoresis and mechanical arts will clearly understand that many variations and modifications are possible in the preferred embodiment without departing from the broader teachings thereof. For example, while the preferred embodiment has been described as having a three axis robot as part of the sample transfer device, it is recognized that the robot may have fewer than three axes. In such a case, the work surface may be mobile with respect to one or two axes. In addition, while the multi-axis robot of the preferred embodiment includes a positional feedback mechanism, the robot may be operated using an open-loop control scheme with no positional feedback, e.g., using stepper motors having step-tracking capability. Furthermore, while the loading wells have been described as having fluid passages to move fluid into and out of the wells, such passages are not required. That is, fluids may be moved into and out of the loading wells using the sample transfer device or other robotic means. Additionally, while the description of the pipette head focused on the use of pipettes to transport fluids, other devices may be also be used, e.g., quills, pins, mechanical grippers and the like. All such variations and modifications are intended to be encompassed within the following claims.

We claim:

1. A sample handling system in a multi-channel capillary electrophoresis apparatus comprising:

a work surface for supporting a plurality of samples located at a plurality of work surface coordinates, wherein the temperature of the work surface is controlled by a temperature controller;

a sample loading assembly comprising a plurality of loading wells;

wherein at least one of the loading wells includes a capillary fixedly positioned therein; and a programmable sample transfer device for transferring a sample from a work surface coordinate to a loading well.

2. The apparatus of claim 1 wherein the work surface comprises one or more tray recesses for accommodating one or more replaceable sample trays.

3. The apparatus of claim 2 wherein the one or more tray recesses comprise a tray locking mechanism.

4. The apparatus of claim 1 wherein the work surface comprises one or more standard wells.

5. The apparatus of claim 1 wherein the sample transfer device comprises a multi-axis robot having an arm.

6. A sample handling system in a multi-channel capillary electrophoresis apparatus comprising:

a work surface for supporting a plurality of samples located at a plurality of work surface coordinates;

a sample loading assembly comprising a plurality of loading wells;

wherein at least one of the loading wells includes a capillary fixedly positioned therein; and a programmable sample transfer device for transferring a sample from a work surface coordinate to a loading well, wherein the sample transfer device includes a pipette head comprising a tip straightener.

7. A sample handling system in a multi-channel capillary electrophoresis apparatus comprising:

a work surface for supporting a plurality of samples located at a plurality of work surface coordinates;

a sample loading assembly comprising a plurality of loading wells, wherein the plurality of loading wells are located in a loading bar which serves as an electrode;

wherein at least one of the loading wells includes a capillary fixedly positioned therein; and a programmable sample transfer device for transferring a sample from a work surface coordinate to a loading well.

8. A sample handling system in a multi-channel capillary electrophoresis apparatus comprising:

a work surface for supporting a plurality of samples located at a plurality of work surface coordinates;

a sample loading assembly comprising a plurality of loading wells, wherein the loading wells are in fluid communication with fluid passages for conducting fluids into and out of the loading wells;

wherein at least one of the loading wells includes a capillary fixedly positioned therein; and a programmable sample transfer device for transferring a sample from a work surface coordinate to a loading well.

9. The apparatus of claim 1 wherein the fluid passages are in fluid communication with a main manifold for supplying fluids and/or vacuum to the loading wells through the fluid passages.

10. The apparatus of claim 9 wherein the fluid passages have in internal diameter from about 0.005 inches to about 0.05 inches.

* * * * *